United States Patent [19]

Müller

[11] 4,119,895
[45] Oct. 10, 1978

[54] BRUSHLESS D.C. MOTOR WITH PRECISE SPEED CONTROL

[75] Inventor: Rolf Müller, St. Georgen, Germany

[73] Assignee: Papst-Motoren KG, St. Georgen, Germany

[21] Appl. No.: 785,725

[22] Filed: Apr. 7, 1977

[30] Foreign Application Priority Data

Apr. 12, 1976 [DE] Fed. Rep. of Germany ....... 2616044

[51] Int. Cl.² .......................................... H02K 29/00
[52] U.S. Cl. .................................... 318/254; 318/138
[58] Field of Search ................ 318/138, 254, 696, 685

[56] References Cited

U.S. PATENT DOCUMENTS

3,999,108  12/1976  Tanikoshi ............................ 318/254

Primary Examiner—Herman J. Hohauser
Attorney, Agent, or Firm—Flynn & Frishauf

[57] ABSTRACT

Speed control for a brushless d.c. motor is made independent of the effects of temperature and aging on the magnetic structure by triggering a rectangular wave pulse generator by voltages produced by the rotation of the motor through a coupling network that makes the trigger time correspond to a certain portion of the rise of voltage so that the influence of the amplitude of the signal on the trigger time will be negligible. The square waves are phase-shifted and integrated to produce a d.c. signal proportional to motor speed on which is superimposed a practically sinusoidal ripple and this signal is fed into a comparator to produce both an error signal from the d.c. component and a commutation control from the a.c. component. The speed is switched between desired precise values by an electronic circuit that controls the duration of the rectangular pulses and makes corresponding adjustments in the integrator and phase shifter.

13 Claims, 6 Drawing Figures

BRUSHLESS D.C. MOTOR WITH PRECISE SPEED CONTROL

This invention relates to a brushless d.c. motor with a permanent magnet rotor and a stator having a winding for generating a torque-producing alternating electromagnetic field as shown in assignee's U.S. Pat. Nos. 3,873,897, 3,840,761 and 3,986,086. The general class of motors of which it is the object of the present invention to provide an improvement is further illustrated by assignee's U.S. Pat. Nos. 3,932,793 and 3,840,761 and application Ser. No. 570,837 owned by the assignee of the present invention, all of which are cross-referenced.

Speed regulated and controlled motors in accordance with the disclosure of U.S. Pat. Nos. 3,873,897 and 3,840,761 have a very simple construction both with respect to the motor structure and with respect to the electronics involved, and for this reason are more economic than the previously conventional brushless d.c. motors with four windings each of which needed to be supplied with current through a separate transistor.

In the case of all brushless d.c. motors, since a voltage indicating the position of the rotor that is needed for speed control must be obtained either from a separate tacho-winding or directly from a motor winding, there is a difficulty arising from the fact that this voltage necessary for speed control depends not only on the speed but also on other factors, particularly on the temperature. The magnetism of the rotor magnets is reduced with increasing temperature and it is also reduced by aging effects. Both of these factors reduce the voltage obtained from the tacho-winding or the motor winding and in the known arrangements accordingly lead to an increase of speed with increasing temperature or with increasing aging of the magnets. The temperature dependence can be partly compensated by means of temperature dependent resistors (compare the resistor 87 in the drawings of U.S. Pat. No. 3,873,897). But this correction is never perfect. The effect of the aging of the rotor magnets can be dealt with by artificial aging before assembling the motor, but this procedure is expensive and therefore used only in precision drives of high value, where the costs involved in artificial aging have little or no consequence.

It is an object of the present invention to provide a brushless d.c. motor with precise speed control that has long-term constancy of its characteristics.

SUMMARY OF THE INVENTION

Briefly, pulses are generated in response to signals derived from the physical movement of the rotor of the motor, which pulses (usually rectangular pulses) have an amplitude and length fully independent of the condition of the motor and particularly of the physical state of the rotor magnets. Since such rectangular pulses are not well suited for speed control, they are then converted into an analog signal having a d.c. component determining the motor speed and a small a.c. component determining the phase relation of the current pulses in the motor relative to the maxima of voltage induced in the motor windings by the rotating rotor magnets, as well as the duration of these current pulses. In this fashion it is possible to regulate motors in accordance with the present invention down to relatively low speed with good regulation quality and long-term constancy of control.

It is particularly advantageous to utilize a circuit of the monostable multivibrator type for generating the pulses and to provide at the input of the monostable multivibrator a coupling network that at least approximately sets the trigger timing to a particular phase angle following the null transition of the voltage detected in the motor, substantially independently of the amplitude of the voltage so detected. The trigger timing, setting the beginning of each pulse, is thus made practically independent of thermal or aging variations in the voltages induced in the motor, and it has been found that with such a coupling network the motor speed can be controlled over a relatively large range without requiring fine adjustment or trimming of the network for precise control. This provides a substantial simplification of the speed control if it is used for setting two or more definite speeds, as is often required in sound recording and sound reproducing service.

It is particularly useful to utilize negative feedback responsive to the motor current that reduces the control magnitude of the speed control circuit in proportion to the magnitude of the motor current. Such a negative feedback makes it possible with the simplest arrangements to stabilize the speed control regulation loop and to make the loop amplification independent of temperature and other disturbing influences.

The invention is described more particularly by way of illustrative and non-limiting examples, with reference to the accompanying drawings, in which.

Figure 1:
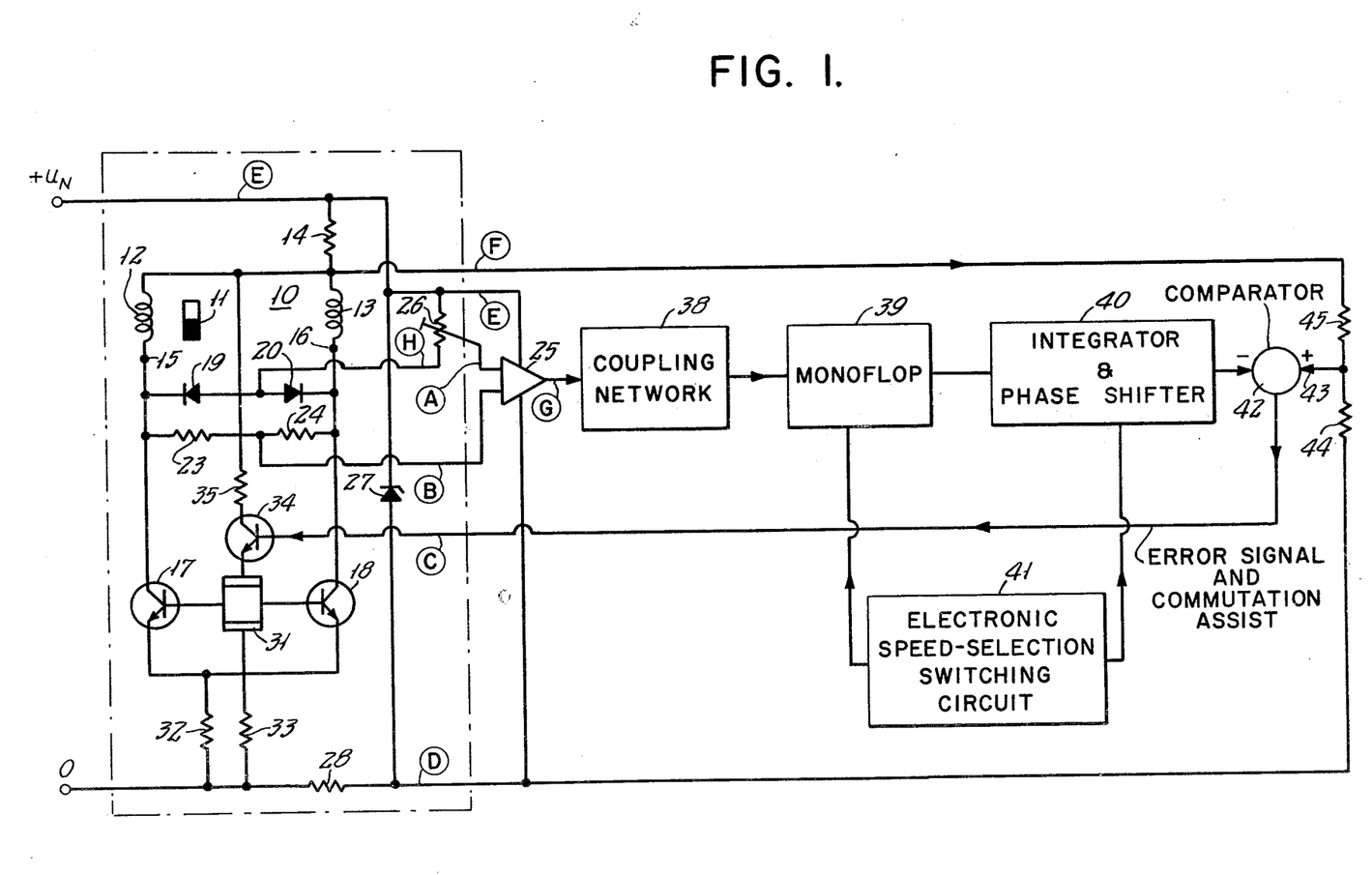
FIG. 1 is a general circuit diagram, partly in block diagram form, of a motor according to the present invention.

FIG. 1 is a block diagram with circuit details, at the left, of a motor as described in the above-identified prior patents and applications and also in German published patent application (AS) No. 2,346,380. The motor represented can be just as well a motor with a flat air gap as a motor with a more or less cylindrical air gap. Such details of the mechanical construction are without significance for the manner of operation of the regulator and speed control. Otherwise stated, the control cannot tell from the signals and voltages supplied to it, what kind of a mechanical motor construction is involved.

The motor 10 has a symbolically indicated permanent magnet rotor 11 and two stator windings 12 and 13 which in operation generate an alternating electromagnetic field, in this case no rotating magnetic field. Both windings are connected through a resistor 14 to a positive supply bus E (e.g., at +30 V with respect to the terminal O). Their other terminals 15 and 16 are respectively connected with the collectors of the npn transistors 17 and 18, and also to the respective cathodes of the diodes 19 and 20 and to one terminal each of a resistor 23, 24, which last are connected together and, in common, through a conductor B to a first input of the amplifier 25. Similarly the anodes of the diodes 19 and 20 are connected together and in common over a conductor H with one terminal of a potentiometer 26, the other terminal of which is connected to the positive supply bus E and the tap of which potentiometer is connected through a conductor A to the other input of the amplifier 25. The amplifier 25 is supplied a voltage stabilized by the Zener diode 27, which is connected between the conductors D and E and has a series resistor 28 connected between the conductor D and the O terminal of the motor. If for example the Zener diode 27 is designed for 20 V and the potential $+U_N$ present on the voltage supply bus E is 30 V, the conductor D has a potential of +10 V with reference to the terminal O. This is important and advantageous for the generation of the control magnitude utilized in the control circuit as will be described below in more detail.

The bases of the transistors 17 and 18 are respectively connected to the outputs of a Hall generator 31, while the emitters of these transistors are connected together and in common over a resistor 32 with the terminal O, to which terminal there is also connected a resistor 33 leading to one of the current terminals of the Hall generator 31. The other current terminal of the Hall generator is connected to the emitter of a control transistor 34 (npn), of which the collector is connected through a resistor 35 with the conductor F.

The entire control circuit is connected to the regulated voltage between the conductors D and E. This is shown in FIG. 1 only for the amplifier 25. The output signal of the amplifier 25 is supplied to a coupling network 38, the output signal of which serves to trigger a monostable multivibrator 39, at the output of which an integrator and phase shift circuit 40 is connected that produces at its output an actual speed signal, which may be referred to as a speed feedback signal, in the form of a d-c voltage on which a ripple of desired phase and amplitude is superimposed, and this combined signal is then supplied to a comparator 42, to the other input 43 of which is supplied a control magnitude (fixed d.c. signal on which a feedback dependent upon motor current is superimposed). For generation of the control magnitude there is provided a voltage divider with a first resistor 44 between the conductor D and 43, a second resistor 45 between 43 and the conductor F, and the resistor 14 between conductors F and E. When there is no motor current flowing, the size of the control magnitude present at 43 is determined simply by the ratio (R14 + R45): (R14 + R45 + R44), and since this voltage divider is supplied with the voltage stabilized by the Zener diode 27, when there is no motor current an unmodified and fixed control magnitude is provided to the circuit point 43. If, however, current flows in the motor 10 and thus through the resistor 14, a voltage drop is produced at the latter resistor and the potential of the conductor F sinks, so that the potential at point 43 also sinks. With increasing motor current the control magnitude therefore becomes smaller and this produces a negative feedback that reduces the loop amplification of the regulation circuit and thereby stabilizes the control circuit. This negative feedback can be set at a desired value in a very simple way by the selection of the resistor 14. Although the motor 10 is supplied with the unregulated voltage between E and O, the voltage divider R14 − R45 − R44 is supplied with the regulated voltage between E and D, and a partial voltage dependent upon motor current exerts an effect on this voltage divider and produces the negative feedback. This is made possible, in a way according to the invention, by the presence of the series resistance 28 of the Zener diode circuit 27 in the negative supply lead of the circuit while the resistor 14 for the negative feedback is, on the other hand, connected to the positive supply lead E. In this manner, as an additional feature of the invention, a direct introduction of the negative feedback voltage in the control loop is made possible.

The output signal of the comparator 42 is supplied over a conductor C to the base of the transistor 34. If the motor speed should be too high, the output signal of the integrator 40 becomes big, the comparator 42 provides a big signal and this blocks the transistor 34 almost completely, so that the Hall generator 31 receives only very little current or none at all and the motor is practically deprived of current, as shown in portion (d) of FIG. 4 by the bottom wave form that is labelled "idling."

The exact manner of operation of the control circuit will presently be described with reference to FIGS. 3 and 4.

For switching the regulated motor speed, for example from 300 to 600 r.p.m., there is provided an electronic speed selection switch 41 which switches over in a contactless manner not only the monostable multivibrator 39 (a circuit sometimes referred to as a monoflop) but also the integrator and phase shifter 40.

There are various ways for deriving a voltage from the motor 10 which is substantially proportional to the motor speed. The illustrated embodiment, the circuit shown in U.S. Pat. No. 3,932,793, is described in great detail in that patent, so that for details regarding the derivation of this voltage, unnecessary bulk in this specification can be avoided by this reference to the disclosure of that patent.

Figure 2:
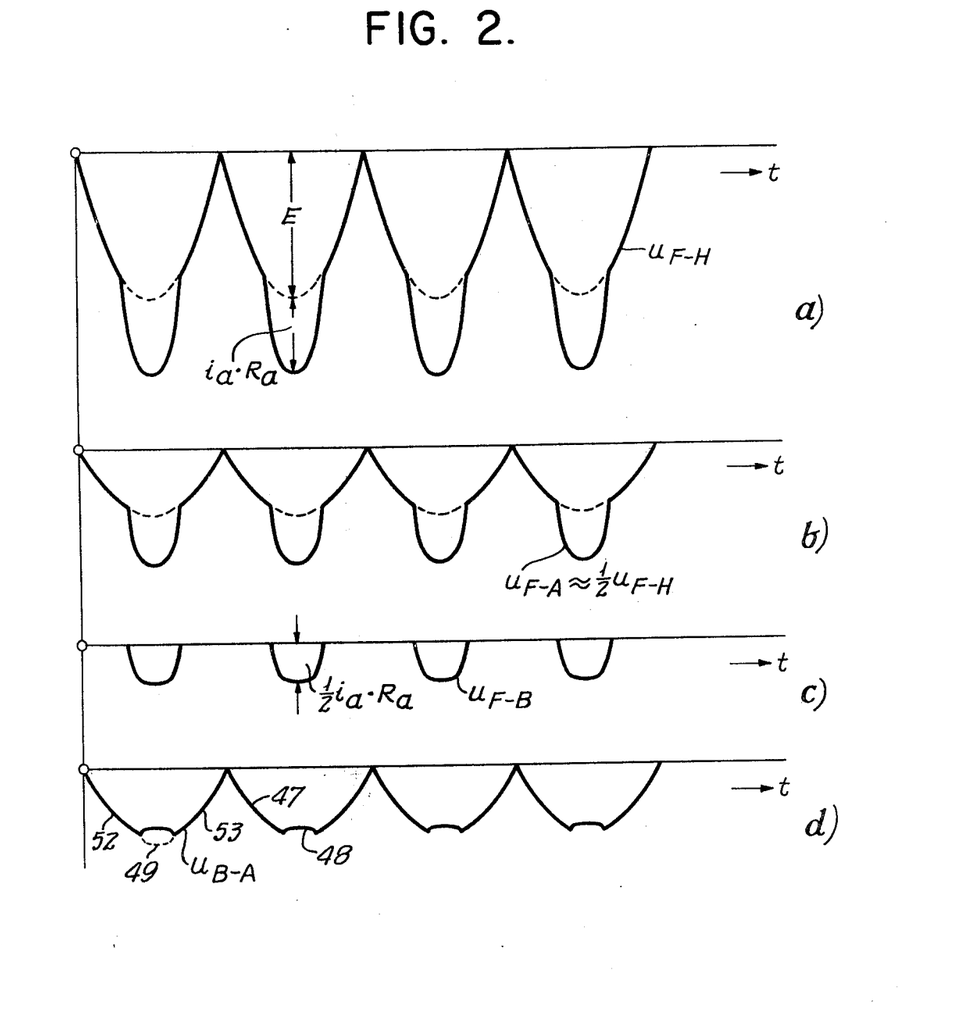
FIG. 2 is a graphical timing diagram for explaining how a voltage dependent upon speed is derived from the motor of FIG. 1.

Portion (a) of FIG. 2 illustrates the voltages that arise in the current carrying windings 12 and 13 in terms of the electromotive force E induced by rotation of the rotor 11 in a winding 12 or 13. $i_a \cdot R_a$ designates the voltage drop produced by the current $i_a$ and the winding resistance $R_a$ in the same winding. When the motor runs slowly (for example 300 r.p.m.) E can typically be about 4 V, and $i_a \cdot R_a$ can be for example about 20 V.

This voltage $i_a \cdot R_a$ has the effect that the conductor B (artificial null point of the system) now receives a negative potential relative to the conductor F, the course of which potential, plotted against time, runs proportionally to $i_a \cdot R_a$, but has only half the magnitude of the latter by the voltage dividing effect of the two equal resistances 23 and 24. This potential accordingly is $0.5 \cdot i_a \cdot R_a$ and is represented in the portion (c) of FIG. 2.

It will be further recognized that the potential of points 15 and 16, except for the voltage drop produced by the armature current, run symmetrically to each other, and that on the conductor B only one signal is present and it is proportional to the voltage drop in whichever winding is passing current.

The voltage $u_{F-H}$ which is represented in portion (a) of FIG. 2, is picked up by the diodes 19 and 20 and is available to the conductor H. By means of potentiometer 26 it is reduced by about half, so that the voltage represented in portion (b) of FIG. 2, which appears at the tap A of the potentiometer 26, is about half of $u_{F-H}$.

This half voltage is supplied over the conductor A to the amplifier 25, and so is the voltage at the conductor B. The amplifier 25 thus evaluates the difference between the two weighted voltages at the conductors H and B. The weighting is carried out by means of the potentiometer 26, for by shifting its tap either the voltage on conductor A or that on conductor B can be made predominant.

For example portion (d) of FIG. 2 shows a case in which the potentiometer 26 tap is put somewhat above the middle position, i.e., the reduction ratio is greater than 2:1, so that at the peak of the half wave represented in portion (d) of FIG. 2 there occurs a dip 48 that becomes greater the greater is the armature current, so that the d.c. component of this voltage 47 is reduced.

If, on the contrary, the reduction ratio is made smaller than 2:1, thus when the potentiometer tap is shifted towards the bottom, a hump 49 is produced on the peaks of the half waves, as shown in broken lines in portion (d) of FIG. 2 at only one of the half waves shown in the figure. Naturally, the potentiometer 26 can also be so adjusted that neither a dip 48 nor a hump 49 is produced, and since the armature current is measured directly at the armature windings, this adjustment holds likewise for all operating conditions of the motor.

At the output of the amplifier 25 there is thus received a signal, the envelope shape of which is determined at least roughly by the voltages E induced in the windings 12 and 13 by the rotor magnet 11. In particular this holds for the null transitions of the voltage 47 illustrated in portion (d) of FIG. 2 and — at any rate during operation — for the rising flanks 52 and the falling flanks 53. The regulation and control circuit according to the invention utilizes the information that is contained in the pulse sequence 47 and the rising flanks 52, since with this flank signal, pulses of constant length and amplitude are triggered at about 45°, 225°, etc. The circuit shown in FIG. 3 serves to produce this effect.

In FIG. 3 the motor 10 is not again shown, but only the conductors B, C, D, E, F, H leading to it are shown which correspond to the similarly designated conductors of FIG. 1. Just as in FIG. 1, the designations 38, 39, 40, 41 and 42 in FIG. 3 respectively designate the coupling network, the monostable multivibrator, the integrator and phase shifter, the electronic speed changing circuit, and the comparator. The resistors 44 and 45, as well as their junction tap 43 for providing the control magnitude, are likewise shown again in FIG. 3.

Figure 3:
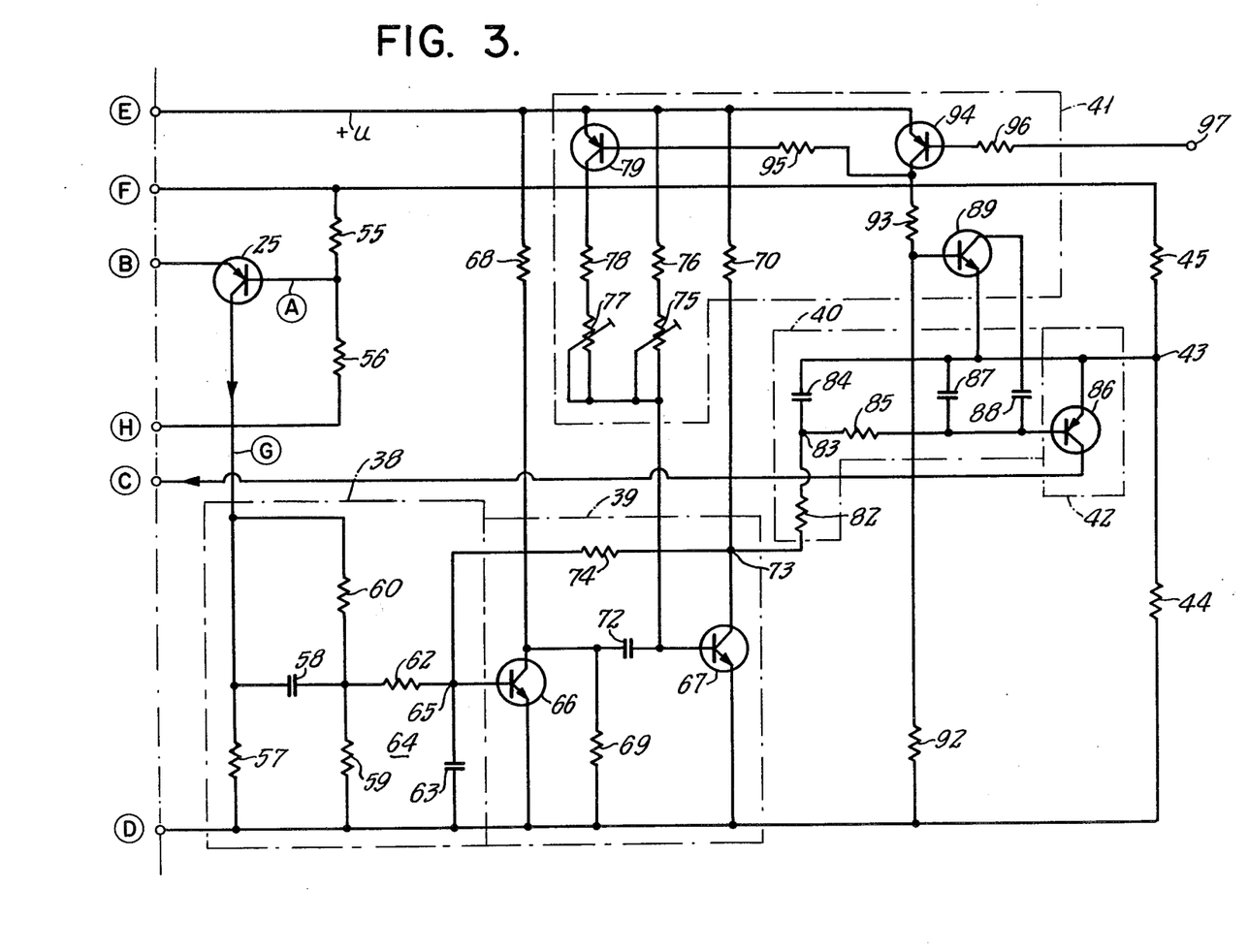
FIG. 3 is a detailed circuit diagram of the speed control portion of the motor of FIG. 1.

The potentiometer 26 is replaced in FIG. 3 by two fixed resistors 55 and 56, of which 55 has the greater resistance, in order to obtain humps 49 (FIG. 2) as described above, which corresponds to the provision of a negative feedback. The tap A is connected to the base of the pnp amplifier transistor 25, of which the emitter is connected to the conductor B and the collector is connected through a resistor 57 with the conductor D. The voltage variations at the resistor 57 accordingly occur in the manner illustrated in portion (d) of FIG. 2, but they are shifted in potential in the negative direction in comparison with the signals at conductor A.

The voltage at the resistor 57 has a d.c. component and an a.c. component. The a.c. component is furnished to a relatively large capacitor 58 and a resistor 59, whereas the d.c. component is supplied over a relatively high resistance 60 also to the resistor 59. By means of 58 and 60 the a.c. and d.c. components are differently weighted. The signal at 59 is then supplied to a phase shifter 64 consisting of a resistor 62 and a capacitor 63 which passes it on to the input 65 of the monoflop 39. The parts 57 to 64 together form the coupling network 38 for the monoflop, which assures that the monoflop 39 will always be triggered in the middle of the flank 52 illustrated in portion (d) of FIG. 2, thus largely independently of the amplitude of the voltage 47. It has been found that with the coupling circuit 38 in the form shown in FIG. 3 such triggering of the monoflop is possible over a wide speed range.

The monoflop 39 contains two npn transistors 66 and 67, both the respective emitters of which are connected with conductor D. The circuit point 65 is connected to the base of transistor 66, while the collector of transistor 66 is connected through a resistor 68 with conductor E, through a resistor 69 with conductor D and through a capacitor 72 with the base of transistor 67, of which the collector is connected with the output 73 of the monoflop 39, through a resistor 74 with the circuit point 65, and through a resistor 70 with conductor E. Furthermore, the base of transistor 67 is connected through a potentiometer 75 and a resistor 76 with conductor E. The base of transistor 67 is connected through a potentiometer 77 and a resistor 78 with the collector of a pnp transistor 79, of which the emitter is connected to conductor E. If 79 is blocked, resistances 75 and 76 are the charging resistances for the capacitor 72 and a relatively long charging time results, and likewise a relatively long pulse duration for the monoflop 39, as is needed at low speeds. If 79 is conducting, the charging resistance for 72 is smaller and the pulse duration is shortened, as is necessary at a higher speed. The circuit point 73, connected to the collector of transistor 67, is connected with the input of the phase shifter and integrator 40 through an input resistor 82 of the latter that connects the circuit point 73 with the circuit point 83, at which are connected together a capacitor 84, the other terminal of which is connected to the tap 43, and a resistor 85, the other end of which is connected to the base of a pnp comparator transistor 86. Between this base and the circuit point 43 at the output side of the phase shifter and integrator is a capacitor 87 and, furthermore, a capacitor 88 is connected between the base of the comparator transistor 86 and the collector of an npn switching transistor 89, the emitter of which, like that of the comparator transistor 86 is connected to the circuit point (voltage divider tap) 43. The base of switching transistor 89 is connected through a resistor 92 with conductor D and through a resistor 93 with the collector of a pnp switching transistor 94, which last is also connected through a resistor 95 with the base of transistor 79, while the emitter of switching transistor 94 is connected to conductor E and its base is connected through a resistor 96 with a terminal 97 that may be designated as a control input for the circuit of FIG. 3.

The transistors 79, 89 and 94 belong to the electronic speed switching circuit 41. When transistor 94 has a negative potential at its input (base), it becomes conducting and thereby blocks transistor 79, so that as above explained, the monoflop 39 is switched to a long pulse duration. Furthermore, transistor 89 then becomes conducting and thereby switches the capacitor 88 (large) in parallel to the capacitor 87 (small) and thereby adjusts the phase shifter 40 to the lower frequency of the pulses produced by the monoflop 39 and to their prolonged duration. Conversely, when a positive potential is provided at the control input 97, the transistors 94 and 89 are blocked, while the transistor 79 becomes conducting and thereby shortens the pulse duration of the monoflop circuit 39.

Figure 4:
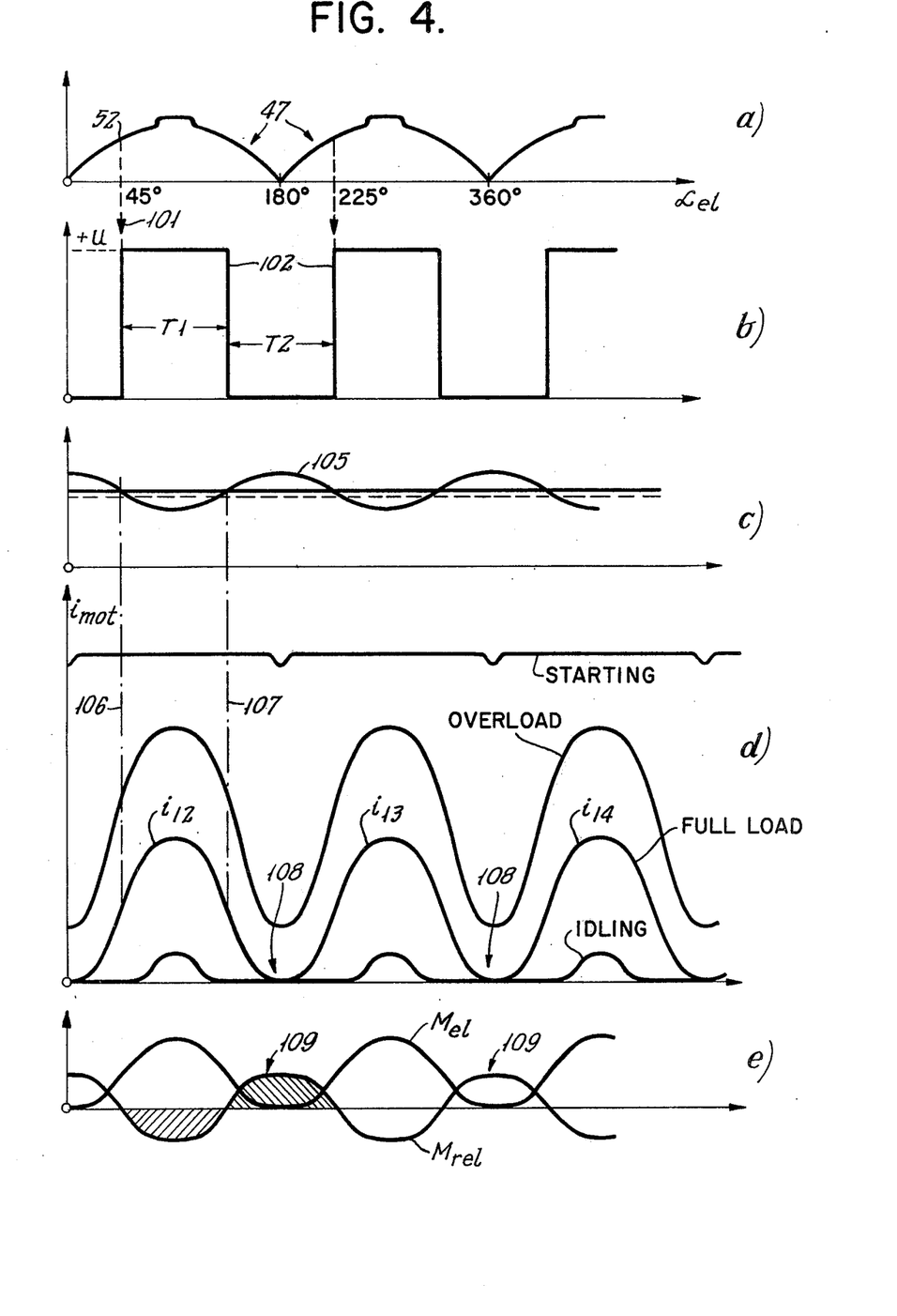
FIG. 4 is a graphical timing diagram for explaining the manner of operation of the motor of FIGS. 1 and 3.

The circuit shown in FIG. 3 works as follows:

There is produced at resistor 59 during operation, as explained, a composite of a d.c. voltage and a voltage that at full load has approximately the form illustrated in portion (a) of FIG. 4. At about 45° of the flank 52 the monoflop 39 is triggered, its capacitor having become charged over the now effective ones of the resistors 75 to 78 and the resistor 69, as indicated by the dashed line 101 in FIG. 4. In this manner the previously blocked transistor 66 is made conducting, and the previously conducting transistor 67 becomes blocked, so that the potential on the collector of the latter jumps from about the potential of the conductor D (e.g., +10 V) to the potential +U of the conductor E (e.g., +30 V), thus a jump of about +20 V. The capacitor 72 now discharges, and when its right-hand electrode has become sufficiently negative, the transistor 67 again becomes conducting and at the same time blocks the transistor 66 over the coupling resistor 74. When this occurs the potential at the output 73 jumps back from, for example, +30 V to +10 V. The pulse duration of the monoflop 39 is thus so fitted to the motor speed that at the desired motor speed the duration T1 of a pulse is always of approximately the same magnitude as the interval T2 between two succeeding pulses (cf. portion (b) of FIG. 4). This means that the pulse duration for an n-pole motor is about 1/2n of the revolution period of the motor, e.g., at 300 r.p.m. or 5 r.p.s. one revolution lasts 200 millisec. and the pulse duration for a six-pole motor is about 200/6.2 msec.

The information from signal 47 illustrated in portion (d) of FIG. 2 or portion (a) of FIG. 4 is thus converted into a sequence of rectangular pulses of exactly determined shape, having a frequency and phase corresponding to those of the signal 47 [cf. portion (b) of FIG. 4 where the output pulses 102 of the monoflop 39 are represented].

These rectangular pulses would be quite unsuitable for a regulating function and must therefore, in accordance with the invention, be transformed into an analog signal of a quite definite form. The circuit 40 is provided for this purpose and in its first stage 82, 84 a more or less triangular voltage is formed from the rectangular pulses 102, the amplitude of the triangular pulses being already substantially smaller than the amplitude of the pulses 102. In the second stage (resistor 85 and capacitor 87 or capacitors 87 and 88 in parallel) an integration of this triangular voltage takes place in which somewhat parabolic voltage rises and falls result. The amplitude of these parabolic voltages 103, that quite closely approach a sinusoidal voltage in shape and are represented in portion (c) of FIG. 4, is again substantially smaller than that of the triangular voltage. In the circuit 40 the amplitude is thus reduced, the phase shifted by 180° (compare portions (b) and (c) of FIG. 4) and the rectangular pulses are converted into a direct current on which is superimposed a more or less sinusoidal a.c. voltage shifted by 180° in phase. The essential in this case is that neither the amplitude of this d.c. voltage nor the amplitude of the a.c. voltage depends in any way whatsoever on the temperature of the motor or on an aging characteristic of the rotor magnet, but both depend only on the sequence of the half waves of the signals 47 in portion (a) of FIG. 4.

The voltage 105 at the output of the phase shifter and integrator 40, thus the d.c. voltage with the superimposed sinusoidal voltage already described, can make the transistor 86 conduct if its base voltage is more negative than its emitter voltage (with an allowance for the threshold voltage of the transistor necessary to produce base current). When the transistor 86 becomes conducting, it supplies base current to the control transistor 34 (FIG. 1) over the conductor C and makes the transistor 34 conducting. If now the motor current rises, thus when a north pole or a south pole of the rotor 7 lies opposite the Hall generator 31, the potential of the point 43 falls as above described, and therefore also the emitter potential of the transistor 86, in step with the motor current, so that the current in the conductor C is reduced, which operates as negative feedback. The sinusoidal components of the voltage 105 have the effect that the motor windings 12 or 13 as the case may be always receive current when the voltage 47 induced in it has a maximum (compare the arrows 106 and 107 in portion (d) of FIG. 4) so that the current in the motor winding 12 is represented by $i_{12}$ and the current in the motor winding 13 is represented by $i_{13}$ in each case for various conditions and modes (idling, full load, overload and starting) in FIG. 4. Particularly in the case of a flat type motor, as is for example shown in FIGS. 1 to 4 of U.S. Pat. No. 3,840,761, it is of very great importance that in normal operation there should be gaps 108 between each of the flows of the motor currents $i_{12}$ and $i_{13}$, since otherwise strong forces perpendicular to the plane of the stator plate of the motor would be exerted on the stator plate during the moment of commutation, which forces in the moment of commutation would change their direction and thereby produce unpleasant motor noise. If, on the other hand, current gaps 108 are provided, these noises disappear. It is further important that the motor current should rise and fall gently. This results in the embodiment here described as the result of the multi-stage phase shifter 40. A mere inversion of the pulses 102, which would also bring a phase shift of 180° and would be easy to produce with digital circuits, would not make possible this desirable result. The temperature dependence of the base-emitter threshold voltage of the transistor 86 is hardly noticeable, because of the relatively large voltages to be compared, and is easily compensated, for example by temperature dependent resistors 44 and 45 in the voltage divider.

Portion (e) of FIG. 4 shows the electromagnetic drive torque $M_{el}$ effective on the shaft of the motor under full load, in the relatively broad gaps 109 of which the driving portion of a reluctance moment $M_{rel}$ is effective, as described in detail in the cross-references.

For a better understanding of the invention, a few additional illustrative values for the circuit according to FIGS. 1 and 3 are provided. The motor 10 is a six-pole motor that runs at a regulated speed of 300 or 600 r.p.m. The voltage between E and O is 30 V, between E and D 20 V. R55 = 7.5 K (K = 1000 ohms), R56 and R57 are both 6.8 K, R14 is 24 ohms (for about 50 mA motor current), R59 is 27 K, R60 is 47 K, C58 is 1 μF, R62 is 100 K, C63 is 10 nF, R82 is 47 K, R85 is 33 K, C84 is 2.2 μF, C87 is 0.5 μF, C88 is 6.8 μF, R45 is 3.6 K, R44 is 2.7 K, R23 and R24 are 6.8 K and transistor 86 is a BC307B. Naturally, for other speeds, other values of the components in the two-stage filter 40, in the monoflop 39 and if necessary also in the coupling network 38 may be necessary. The values given above are to be understood as only an example for illustration.

The invention makes it possible to provide a brushless d.c. motor with a highly accurate speed control which has a simple construction and constitution and that has good regulation especially at low speed when loaded with a heavy rotor, and the quality of speed regulation has a very good constancy with time. Furthermore, this desirable result is obtained with a surprisingly simple combination of digital and analog electrical circuit techniques. The motor of this invention is particularly well suited for direct drive of the shaft of a cassette tape recorder, for example in language teaching laboratories. Of course, although the invention has been described with respect to a specific illustrative embodiment, variations and modifications are possible within the inventive concept, for example application of the invention to multi-phase motors that produce a rotating field.

Figure 5:
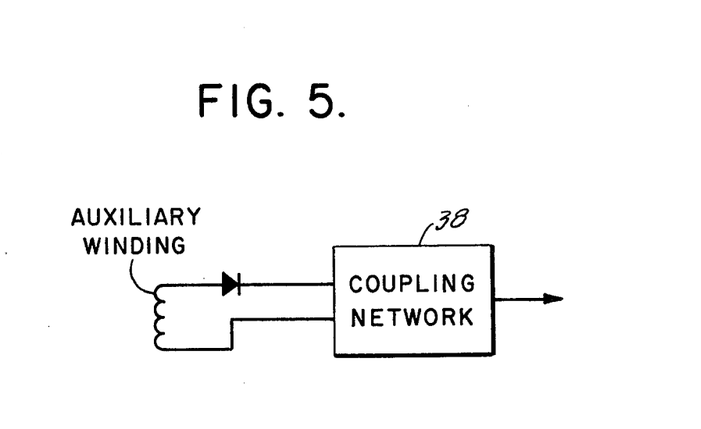
FIG. 5 is a diagram illustrating the use of an auxiliary winding for deriving a signal indicative of speed of the motor for supply to the speed control circuit.

The voltage 47 can, for example, also be taken by half-wave rectification of the output of a separate tacho-winding in the motor, as illustrated in FIG. 5. Such a winding can be conveniently so arranged that a phase shift of 180° is no longer necessary in the phase shifter 40, but only a smaller phase shift, for example 90°. Care must be taken, however, that the frequency of the voltage provided by the tacho-winding is the same as the frequency of the voltage 47, because for other purposes it is common in the use of a tacho-generator to make the frequency of the tacho-voltage as high as possible.

Figure 6:
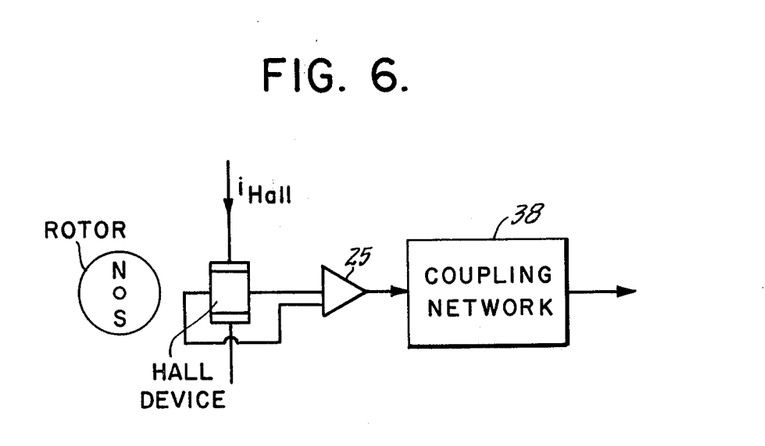
FIG. 6 is a diagram illustrating the use of a galvanomagnetic sensor for deriving a voltage indicative of the speed of the motor for use in the speed control circuit.

Instead of a tacho-voltage, there can be used within the scope of the present invention means to take trigger pulses directly from the motor (for the monoflop 39) with the correct frequency and phase, for example optical or galvanomagnetic signal transmitters, as illustrated in FIG. 6 for the case of a Hall generator. This is particularly useful in motors in which the speed must be controlled over a relatively wide speed range, but of course the fabrication of sensors and their installation in the motor involves substantial additional costs, something that is avoided in the form of the invention illustrated in detail in the present specification.

I claim:

1. A brushless d.c. motor comprising
a permanent magnet rotor;
a stator having a winding;
means supplied with d.c. current and connected to said stator winding for producing an alternating magnetic field in said stator and having a speed control circuit;
means for deriving, from said motor, signals synchronized with the rotation of said rotor;
means for generating pulses of a predetermined length;
means for triggering the generation of said pulses by said pulse generating means in response to said signals;
analog circuit means for phase-shifting and smoothing said pulses
for deriving from said pulses a smoothed voltage having a d.c. component and a superimposed a.c. component, and
means for feeding said smoothed voltage to said speed control circuit for controlling the speed of said motor by said d.c. component of said voltage while the a.c. component serves to control the armature current and torque cycles as the motor turns.

2. A brushless d.c. motor as defined in claim 1, in which said phase-shifting and pulse-smoothing comprise an RC network producing at its output said phase-shifted smoothed voltage.

3. A brushless d.c. motor as defined in claim 1, in which said signal deriving means are means for deriving said signals from said stator winding.

4. A brushless d.c. motor as defined in claim 1, in which said signal deriving means comprise an auxiliary motor winding and means for deriving said signals from said auxiliary motor winding.

5. A brushless d.c. motor as defined in claim 1, in which said motor comprises rotor position sensing means and in which said signal deriving means are means for deriving said signals from said sensing means (FIG. 6).

6. A brushless d.c. motor as defined in claim 1, in which said pulse generating means comprises a monostable multivibrator circuit (39) and a coupling network (38) connected to the input of said monostable multivibrator circuit for setting the triggering instant (101) of said multivibrator circuit at a predetermined phase angle after the null transition of a signal voltage (47) taken from a winding of said motor in a manner at least approximately independent of the amplitude of the voltage (47) derived from said motor winding.

7. A brushless d.c. motor as defined in claim 6, in which said coupling network (38) comprises a first coupling member (58) for transmitting the a.c. voltage component of a voltage derived from said motor and a second coupling member (60) for transmitting the d.c. component of the voltage derived from said motor and comprises also a phase shifter (64).

8. A brushless d.c. motor as defined in claim 1, in which there is provided electronic switching means for switching between predetermined motor speeds, said switching means being contactless means for changing the duration of the output pulses of said pulse generator and for changing the parameters of said phase shifter (40).

9. A brushless d.c. motor as defined in claim 8, in which said electronic switching means (41) comprises a transistor (89) of which the emitter-collector path is connected in series with a supplementary capacitor (88) of said phase shifter (40) in such a way that when said transistor is in conducting condition, said supplementary capacitor (88) of said phase shifter (40) is operative in said phase shifter.

10. A brushless d.c. motor as defined in claim 1, in which means are provided for effecting negative feedback (14) dependent upon the amount of current flowing in said motor, said negative feedback means being connected so as to reduce a control voltage applied to said speed control circuit in proportion to the magnitude of said motor current.

11. A brushless d.c. motor as defined in claim 10, in which said negative feedback means comprises a comparator (42, 86) having an input connected to the output voltage of said phase shifter (40) and another input connected to a tap (43) of a voltage divider (14, 45, 44) supplied with a substantially constant d.c. voltage and having a component resistor (14) thereof connected so that the motor current flows therethrough, said component resistor being so connected in said voltage divider as to provide a negative feedback potential for said motor at said tap (43) when motor current is flowing.

12. A brushless d.c. motor as defined in claim 1, in which the duration of the respective pulses produced by said pulse generator is approximately $1/2n$ of the rotation period of the motor, where $n$ is the number of poles of the motor.

13. A brushless d.c. motor as defined in claim 12, in which the motor has at least three pairs of poles.